United States Patent [19]

Khattak

[11] Patent Number: 4,788,859

[45] Date of Patent: Dec. 6, 1988

[54] METHOD AND APPARATUS FOR DETERMINING DEFLECTION IN PAVEMENT

[76] Inventor: Anwar S. Khattak, 612 S. Lincoln, Spokane, Wash. 99204

[21] Appl. No.: 120,066

[22] Filed: Nov. 13, 1987

[51] Int. Cl.$^4$ .............................................. G01B 5/30
[52] U.S. Cl. .................................... 73/146; 356/356; 356/375; 364/550
[58] Field of Search .................... 73/146, 104, 105; 33/551; 364/550; 356/356, 371, 375; 250/234, 235

[56] References Cited

U.S. PATENT DOCUMENTS

| | | | |
|---|---|---|---|
| Re. 27,875 | 1/1974 | Swift | 73/146 |
| 4,456,829 | 6/1984 | Fohey | 250/235 |
| 4,571,695 | 2/1986 | Elton et al. | 364/550 |

Primary Examiner—Donald O. Woodiel
Attorney, Agent, or Firm—Wegner & Bretschneider

[57] ABSTRACT

A method for direct measurement of the vertical displacement of a point on the surface of pavement upon application of a load thereto is disclosed. This method measures the vertical displacement through the use of optical equipment. Specifically, the displacement is equivalent to the vertical movement of an optical focusing element between the position of the element when a point on the surface of the pavement is in focus with and without the application of the load. This point linear displacement measurement can also be applied to the calculation of a volumetric displacement. An apparatus capable of carrying out these methods is also described.

19 Claims, 2 Drawing Sheets

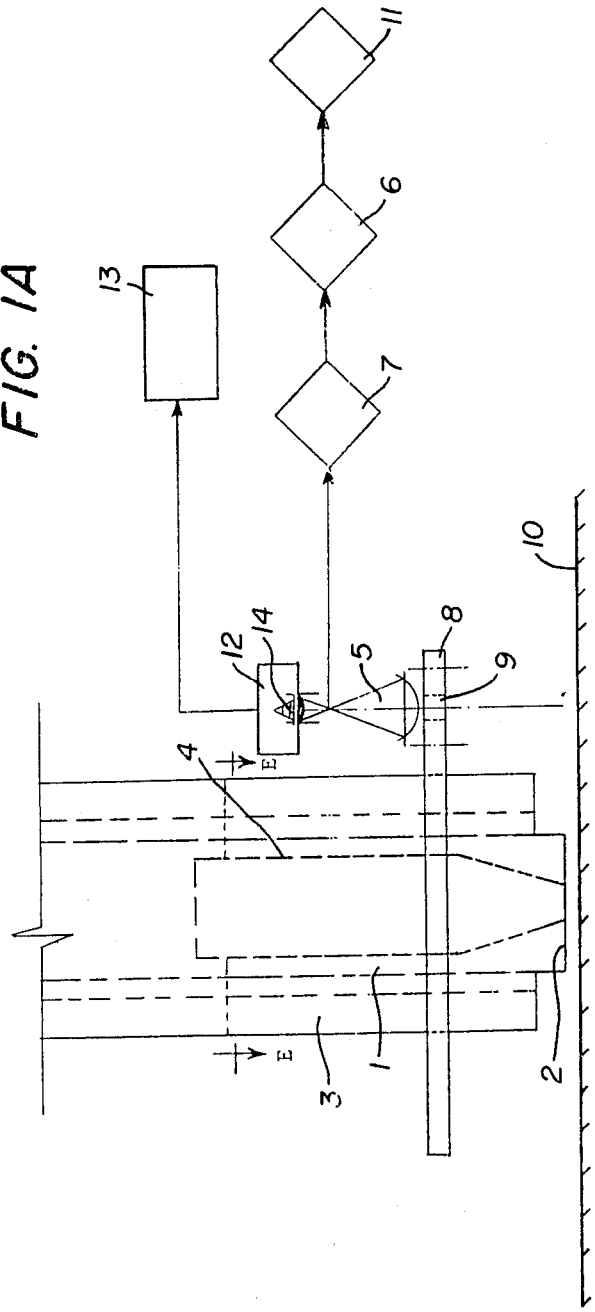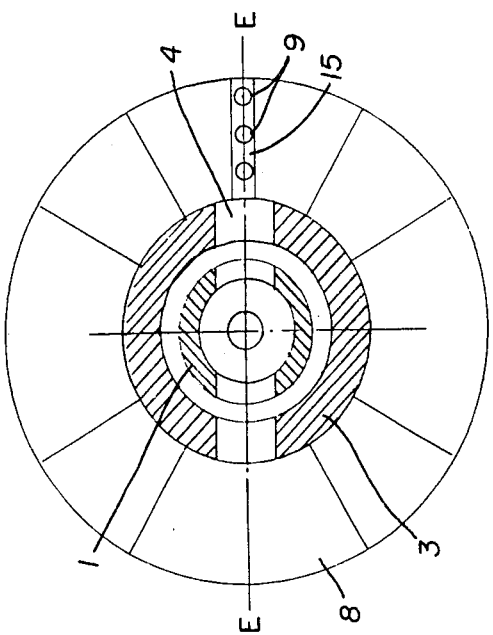

METHOD AND APPARATUS FOR DETERMINING DEFLECTION IN PAVEMENT

BACKGROUND OF THE INVENTION

The spring constant or reaction modulus is an important parameter for the engineering considerations involved with materials such as pavement. In pavement engineering, for example, highway and airport runway pavement slabs rest on an elastic foundation. Typically, pavement rests on a base, one or more sub-bases and the natural ground. A defect that arises in one of these layers manifests itself in an alteration of the spring constant of the pavement long before any surface pavement damage can be spotted. Thus, a determination of this parameter for an existing pavement portion is essential for the analysis and design of future top asphalt/concrete layers and the determination of the necessity of such repair work.

Time consuming and expensive plate load tests are currently used for the determination of the modulus of subgrade reaction. This plate load test is commonly used, but the parameters obtained therefrom are merely approximations and the procedure damages the pavement surface tested. As a result, there exists a need for a non-destructive method and, therefore, an apparatus that can be used to determine the spring constant or reaction modulus rapidly and accurately without damage to the pavement surface. Other methods for determining pavement deflection use lever systems or operate on a vibratory force principle.

SUMMARY OF THE INVENTION

The present invention involves the application of a predetermined load on a rigid pavement supported by subgrade layers, i.e. base, sub-base and natural ground. Such an application causes vertical displacements of all surface points located within the effective zone in the proximity of the applied load. The deformation of the pavement surface created by the application of the load is the deflection basin. Each of the point vertical displacements contributes to the volumetric displacement defined by the deflection basin. This volumetric displacement must be calculated to determine the spring constant of the pavement system. The spring constant is defined using the spring equation as follows:

$$k = \frac{\text{load applied}}{\text{volumetric displacement}}$$

The present invention facilitates the direct measurement of deflection and hence the determination of the volumetric displacement of the pavement resulting from the application of a predetermined load. Thus, the spring constant can be determined quickly and accurately.

BRIEF DESCRIPTION OF THE DRAWINGS

FIG. 1A illustrates a front view of an exemplary apparatus of the present invention.

FIG. 1B illustrates a top view of an exemplary apparatus of the present invention.

DETAILED DESCRIPTION OF THE INVENTION

Figure 2:
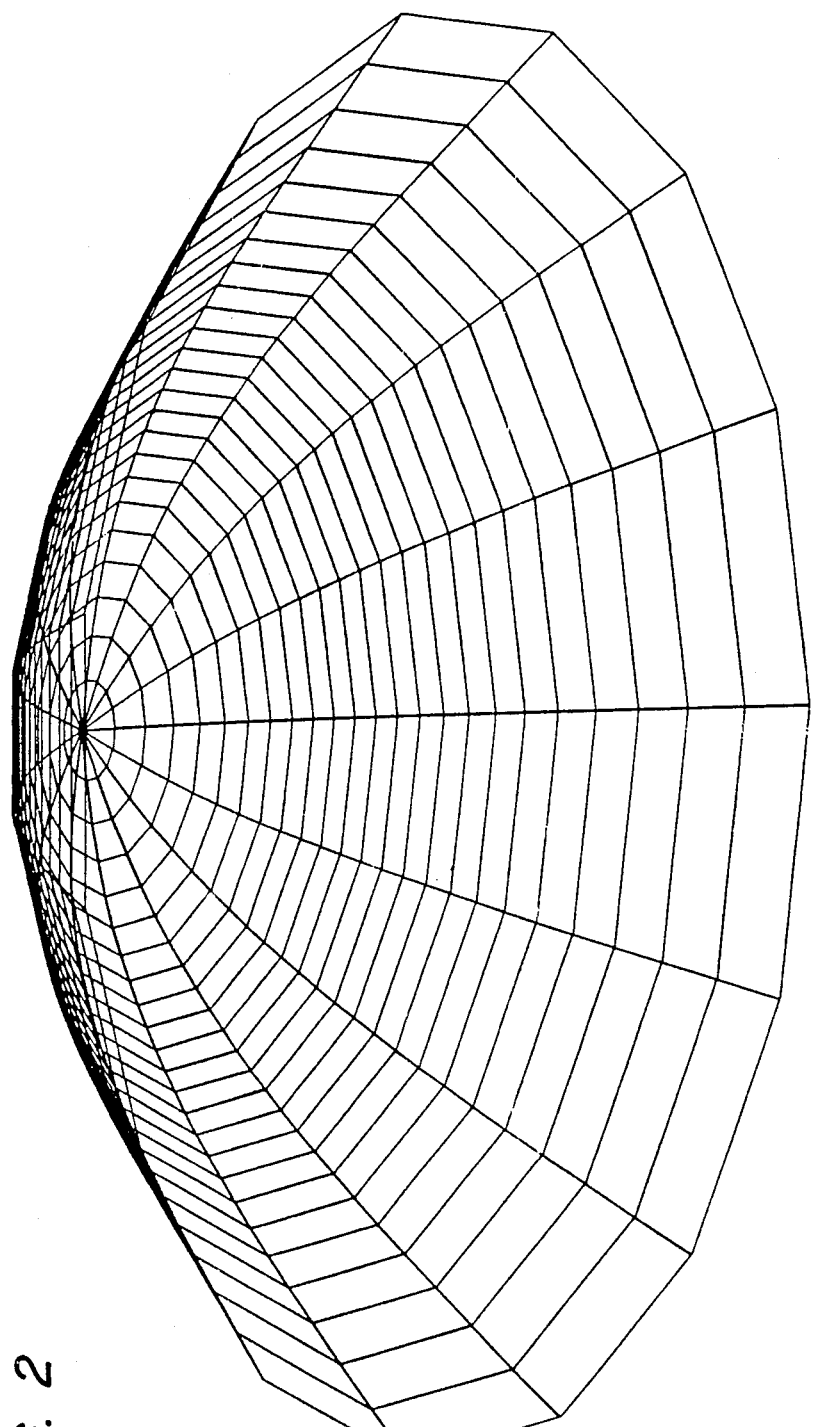
FIG. 2 illustrates a sample deflection basin obtainable from the operation of the present invention.

The first aspect of the present invention provides a method of directly measuring vertical displacement of pavement which comprises:
 (a) placing an optical unit having a focusing element in a fixed position above the pavement, wherein said unit is capable of being focused upon the pavement;
 (b) focusing said optical unit on said pavement at a time prior to application of a predetermined load on said pavement, and recording a first position of the focusing element when said optical unit is focused on said pavement;
 (c) focusing said optical unit on said pavement at a time when a predetermined load is applied to said pavement, and recording a second position of the focusing element when said optical unit is focused on said pavement; and
 (d) measuring the difference between the first and second positions of the focusing element,
wherein said difference represents the vertical displacement of the pavement.

By vertical displacement, there is contemplated the vertical distance moved by a point on the surface of the pavement in response to the application of a predetermined load thereto.

By an optical unit, there is contemplated an optical device having a focusing element or means and a vertical displacement measuring means. That is, the optical unit must be capable of bringing a point on a target into focus both before and during the application of a predetermined load thereto. The optical unit will bring the surface point into focus through a vertical or other movement of the focusing element.

The optical unit must further be capable of measuring the vertical displacement of (or other movement of) the focusing element between the first and second focusing positions detailed in steps (b) and (c) above. If the focusing element functions on a vertical displacement principle, that vertical displacement of the focusing element between its position corresponding to the focused image prior to the application of the load and its position corresponding to the focused image during the application of the load will be equal to the vertical displacement of the pavement at that point.

Within this optical unit, conventional optical equipment having focusing elements may be used. For example, stereomicroscopes available on the market, such as the Bausch and Lomb Stereozoom TM series or the Reichert Stereostar TM series, may be used in the present invention.

However, in the present invention conventional optical equipment having focusing elements must be modified to include a vertical displacement measuring means. Displacement of the focusing element can be measured in a variety of ways and any method permitting such measurements is contemplated by the present invention. Exemplary of functional displacement measuring means are micrometers, vernier calipers and automatic sensors. These elements are prerequisites of the recording portion of steps (b) and (c).

By a predetermined load, there is contemplated a load sufficient to result in a measurable displacement (typically from about 1/100 mm to 5 mm) of the pavement surface without unduly stressing the pavement. As a result, the predetermined load on the pavement can be expressed as a total load (pressure) or in terms of stress (pressure per unit area). Exemplary loads usable in the present invention are between about 9,000 and about 50,000 pounds. Exemplary stresses are between about 1,000 and 3,000 pounds/inch$^2$. The stresses necessary to achieve a measurable displacement of a specific pavement will depend on the structure thereof, which in turn will depend on the stresses to be withstood by the pavement during its normal use. As a result, higher loads will be required to assess the state of pavement used for airport runways than that used in parking lots, for example.

The method of the first aspect of the invention can be carried out manually and with relative ease by an operator using the apparatus of the second aspect of the present invention. However, the convenience of the displacement measuring method can be enhanced by placing any or all of the methodology under microprocessor control. That is, any combination of the operation of the optical unit, the operation of the displacement measuring means within the optical unit, and the final measurement of the difference between the recorded positions can be microprocessor controlled. A preferred embodiment of the present invention provides that the focusing steps (b) and (c) are controlled by a microprocessor. That is, the focusing of the focusing element and the recordation of the positions of that focusing element prior to and during application of a predetermined load are accomplished automatically through microprocessor control.

Another preferred embodiment of the present invention provides that the difference between said first and second positions of the focusing element is measured by a sensor. This, as well as the previous computer-controlled focusing feature, enhances both the speed and the accuracy of the measurements obtained through the use of the method of the first aspect of the present invention.

While a typical application would involve the recordation of the position of the focusing element during sequential focusing of the element on the unloaded pavement prior to that of the loaded pavement, it should be understood that the displacement could be measured in the opposite manner. That is, the method could be conducted as described above with the exception that step (c) could occur prior to step (b).

A second aspect of the present invention provides an apparatus for determining deflection in pavement which comprises:

a load ram element;
and at least one optical unit positioned at a radial distance r from the center of the load ram element and at a height z above the pavement having a focusing means and a vertical displacement measuring means for determining data points indicative of said deflection of the pavement upon application of a load,
whereby the vertical displacement of the pavement is measured by sequentially focusing said optical unit on said pavement both prior to and during said application of a load.

By pavement deflection, there is contemplated both point and area deformation. That is, both linear displacement of a point on the pavement surface and volumetric displacement of an area of the pavement surface can be measured using the apparatus of the present invention, as described in the first and third aspects of the invention.

By a load ram element, there is contemplated an element capable of applying a predetermined load to the pavement surface. Such ram elements for applying a predetermined load to a surface are known in the art, and conventional types can be used in the practice of the present invention. The movement of the load ram may be governed by a hydraulic pressure system. In an embodiment of the invention, the load ram has a slot in the portion of the load ram which contacts the pavement surface, the contacting portion, so that a measurement of the vertical displacement of the pavement at the base of the deflection basin may be obtained. A measurement at the base enhances the accuracy of volumetric displacement measurements obtained by the method of the third aspect of the present invention. The desirability of this measurement may further require the load ram element to be hollow to some degree in the area of the ram element immediately above the contacting portion, to allow the insertion of an optical unit therein.

Preferably, the load ram element is configured such that the cross-sectional area of the contacting portion thereof is sufficient to reduce the stress on the surface of the pavement resulting from the application of the load thereto. To permit this stress reduction and the base measurement discussed above, the load ram is equipped with a hollow bore in the center thereof. This normally involves some tapering of the bore of the load ram element to achieve an increased surface area of the element at the contacting surface. Such a configuration is sometimes referred to as an "upset end".

The optical unit has been discussed above. The location in space of the optical unit is at a distance (z) above the pavement, at a radial distance outward (r) from the central point of the load ram element and at an angular distance (theta) from other optical units or other positions of the same optical unit. This optical unit will measure the vertical displacement of the point on the pavement surface at the same point in the (r,theta) plane. This measurement is obtained by a comparison of the difference between the z value of the position of the focusing element of the optical unit prior to or following the application of a predetermined load to the pavement and the z value of the position of the focusing element during the application of the load.

To permit measurement of the vertical displacement of the pavement at a number of points sufficient to reconstruct the deflection basin produced by the application of the predetermined load, the optical unit may be capable of radial and/or angular motion about the load ram element. Conventional means to permit this type of movement of the optical unit are available and can be employed in the practice of the present invention.

Alternatively, a plurality of optical units may be employed at various specified positions in the (r,theta) plane at a height z above the surface of the pavement. These optical units may also be capable of radial and/or angular movement as described above. Of course, the range of motion required in this embodiment would be less than in the embodiment described previously.

The number of data points obtained directly influences the accuracy of the measurements. That is, an increase in the number of data points results in an increase in accuracy. However, practical limits can be placed on the number of points tested to preserved both the speed and accuracy of the measurements without unduly constraining the design of the apparatus. For example, the measurement of from about 10 to about 60 data points should be sufficient to calculate the volumetric displacement of pavement caused by the application of a predetermined load. Exemplary of the angular dispersion of such points about the load ram is that a measurement should be taken from about every 10 to about every 30 degrees. From about 1 to about 4 points along each radius defined by these angles could be measured.

In a preferred embodiment of the present invention the focusing means is a stereomicroscope. Exemplary stereomicroscopes are discussed above.

In another preferred embodiment of this aspect of the present invention, the vertical displacement measuring means is a micrometer. Another embodiment features a vernier caliper as a vertical displacement measuring means. Also, automatic sensor devices are contemplated as vertical displacement measuring means in an additional embodiment.

The apparatus of this aspect of the present invention is further described in FIG. 1A. Load ram element 1 having an upset end 2 is enclosed within an outer shell 3. Outer shell 3 can optionally have vertical and rotational movement capability. The load ram element 1 has static and dynamic loading capability. Load ram element 1 also has a slot 4 to allow optical unit access to the center of the deflection basin.

A zoom stereomicroscope 5 having manual and/or autofocusing capability and having a micrometer sensor 6 to measure the vertical displacement of the focusing element 7 is supported on a motor driven rotating platform 8 attached to the outer shell 3. This rotating platform is provided with scanning ports 9, i.e. holes in the platform dispersed angularly and radially to allow access of the stereomicroscope 5 to the pavement 10. A microprocessor 11 is operably connected to the optical unit (composed of the stereomicroscope 5 and the micrometer sensor 6) to allow the control and/or data extraction and manipulation functions of the computer to take place.

Additional features such as a camera 12 operably connected to the microscope to facilitate remote viewing of the target area of the pavement through a television monitor 13 and a light source 14 to assure illumination of the target area of the pavement surface during operation of the apparatus are also depicted.

FIG. 1B depicts the platform 8 having scanning ports 9 dispersed in a guide rail 15. The guide rail serves to aid the movement of the stereomicroscope (not shown) to achieve translatory motion along a fixed angle. As described with respect to FIG. 1A, the platform 8 surrounds an outer shell 3, which in turn surrounds a load ram element 1.

A third aspect of the present invention provides a method of determining volumetric displacement of pavement which comprises:
(a) placing an optical unit having a focusing element at plurality of fixed positions (r,theta,z) in the (r,theta) plane above corresponding points in the (r,theta) plane of the pavement (r,theta,z°), wherein said unit is capable of being focused upon the pavement;
(b) focusing said optical unit on the points (r,theta,z°) on said pavement at a time prior to application of a predetermined load on said pavement, and recording a first position of the focusing element of the optical unit at each point in the (r,theta) plane when said optical unit is focused on said pavement;
(c) focusing said optical unit on the points (r,theta,z°) on said pavement at a time when a predetermined load is applied to said pavement, and recording a second position of the focusing element of the optical unit at each point in the (r,theta) plane when said optical unit is focused on said pavement;
(d) measuring the difference between the first and second positions of the focusing element at each point in the (r,theta) plane; and
(e) determining the volumetric displacement for a deflection basin described by the differences calculated in step (d).

By volumetric displacement, there is contemplated the volumetric displacement in the pavement produced by the application of a predetermined load thereto. In other words, the vertical displacement of the surface area of the pavement (a collection of discrete points in a plane) is measured.

The placement of the optical unit at a plurality of fixed points (r,theta,z) contemplates the placement of the optical unit in a plane having radial coordinates (r,theta) at a height z above the pavement surface. The (r,theta) plane of the optical unit is parallel to the (r,theta) plane of the pavement surface. Any height z that would not preclude the focusing of the optical unit upon the pavement surface with and without a load applied thereto could be used in the present invention. Exemplary of convenient heights for carrying out the present invention are from about 0.5 to about 4.5 inches. The level of the surface of the pavement in the z direction is described as z°.

The volumetric displacement calculation involves an additional step beyond the measurement of the point vertical displacements. That is, the volumetric displacement is calculated through the use of the vertical displacement data for each point in the (r,theta) plane where the vertical displacement was measured. Typically, a graphical depiction of the deflection basin is generated. A sample of such a graphical depiction is shown in FIG. 2. Then a mathematical equation is fitted to the surface of the basin. Using the equation and the generated data, the volumetric displacement is calculated. This operation is more quickly and accurately accomplished with the aid of an on board computer.

As described above, any combination of the functions of the apparatus, the operation of the optical unit, the operation of the displacement measuring means within the optical unit and the determination of the point vertical displacement values, can be microprocessor controlled. As a result, preferred embodiments of the present invention contemplate a method of determining volumetric displacement of pavement, wherein the focusing steps (b) and (c) are controlled by a microprocessor through an autofocusing device; the measurement of the difference between the first and second positions of the focusing element is done by a sensor with the measurements optionally inputted into a microprocessor; and/or the volumetric displacement is calculated by a computer with appropriate software.

While a typical application would involve the measurement of the position of the focusing element of the unloaded pavement prior to that of the loaded pavement, it should be understood that the displacement could be measured in the opposite manner. That is, the method could be conducted as described above with the exception that step (c) could occur prior to step (b).

What is claimed is:

1. A method of directly measuring vertical displacement of pavement which comprises:
   (a) placing an optical unit having a focusing element in a fixed position above the pavement, wherein said unit is capable of being focused upon the pavement;
   (b) focusing said optical unit on said pavement at a time prior to application of a predetermined load on said pavement, and recording a first position of the focusing element when said optical unit is focused on said pavement;
   (c) focusing said optical unit on said pavement at a time when a predetermined load is applied to said pavement, and recording a second position of the focusing element when said optical unit is focused on said pavement; and
   (d) measuring the difference between the first and second positions of the focusing element, wherein said difference represents the vertical displacement of the pavement.

2. A method of claim 1, wherein said focusing steps (b) and (c) are controlled by a microprocessor.

3. A method of claim 1, wherein the difference between said first and said second positions of the focusing element is measured by a sensor.

4. A method of claim 1, wherein step (c) occurs prior to step (b).

5. An apparatus for determining deflection in pavement which comprises:
   a load ram element;
   and at least one optical unit positioned at a radial distance r from the center of the load ram element and at a height z above the pavement, having a focusing means and a vertical displacement measuring means for determining data points indicative of said deflection of the pavement upon application of a load, whereby the vertical displacement of the pavement is measured by sequentially focusing said optical unit on said pavement both prior to and during said application of a load.

6. An apparatus of claim 5, wherein said focusing means is a stereomicroscope.

7. An apparatus of claim 5, wherein said vertical displacement measuring means is a micrometer.

8. An apparatus of claim 5, wherein said vertical displacement measuring means is an automatic sensor.

9. An apparatus of claim 5, wherein said vertical displacement measuring means is a vernier caliper.

10. An apparatus of claim 5, wherein said contacting portion of said load ram element has a cross sectional area sufficient to minimize stress on the surface of the pavement resulting from the application of a load thereto.

11. An apparatus of claim 5, wherein said optical unit is capable of radial and angular movement about the load ram element.

12. An apparatus of claim 5 wherein a plurality of optical units are positioned at specified points in the (r,theta) plane at a height z above the surface of the pavement.

13. An apparatus of claim 5, which further comprises a microprocessor operably connected to the optical unit to permit microprocessor control thereof.

14. An apparatus of claim 5, wherein said load ram element has a slot in the contacting portion thereof.

15. A method of determining volumetric displacement of pavement which comprises:
   (a) placing an optical unit having a focusing element in a plurality of fixed positions (r,theta,z) in the (r,theta) plane above corresponding points in the (r,theta) plane of the pavement (r,theta,z°), wherein said optical unit is capable of being focused upon the pavement.
   (b) focusing said optical unit on the points (r,theta,z°) on said pavement at a time prior to application of a predetermined load on said pavement, and recording a first position of the focusing element of the optical unit at each point in the (r,theta) plane when said optical unit is focused on said pavement;
   (c) focusing said optical unit on the points (r,theta,z°) on said pavement at a time when a predetermined load is applied to said pavement, and recording a second position of the focusing element of the optical unit at each point in the (r,theta) plane when said optical unit is focused on said pavement;
   (d) measuring the difference between the first and second positions of the focusing element at each point in the (r,theta) plane; and
   (e) calculating the volumetric displacement for a deflection basin described by the differences generated in step (d).

16. A method of claim 15, wherein said focusing steps (b) and (c) are controlled by a microprocessor.

17. A method of claim 15, wherein the difference between said first and said second positions of the focusing element is measured by a sensor and inputted into a microprocessor.

18. A method of claim 15, wherein the volumetric displacement is calculated by a microprocessor.

19. A method of claim 15, wherein step (c) occurs prior to step (b).

* * * * *